United States Patent [19]

Arnold et al.

[11] 4,190,768
[45] Feb. 26, 1980

[54] DETERMINING THE WATER CUT AND WATER SALINITY IN AN OIL-WATER FLOW STREAM BY MEASURING THE SULFUR CONTENT OF THE PRODUCED OIL

[75] Inventors: Dan M. Arnold; Harry D. Smith, Jr., both of Houston, Tex.

[73] Assignee: Texaco Inc., White Plains, N.Y.

[21] Appl. No.: 920,569

[22] Filed: Jun. 29, 1978

[51] Int. Cl.$^2$ .................. G01V 5/00; G01N 23/00
[52] U.S. Cl. .................................. 250/270; 250/359
[58] Field of Search ............... 250/269, 270, 301, 358, 250/359, 360, 356, 435

[56] References Cited

U.S. PATENT DOCUMENTS

| | | | |
|---|---|---|---|
| 3,240,938 | 3/1966 | Hall, Jr. ............................... | 250/270 |
| 3,263,082 | 7/1966 | Caldwell ............................. | 250/269 |
| 3,521,064 | 7/1970 | Moran et al. ...................... | 250/269 |

Primary Examiner—Davis L. Willis
Assistant Examiner—Janice A. Howell
Attorney, Agent, or Firm—Carl G. Ries; Thomas H. Whaley; William J. Beard

[57] ABSTRACT

Fluid in a pipeline or container at a refinery or at any of various petroleum producing operations is bombarded with neutrons and high energy gamma rays resulting from capture of thermal neutrons are detected. The spectra of the detected gamma rays are then analyzed to determine the relative presence of the elements sulfur, hydrogen and chlorine. From the sulfur measurement, the oil cut of the fluid is determined, enabling the water cut to be determined. From the determined water cut, water salinity can also be determined.

26 Claims, 5 Drawing Figures

DETERMINING THE WATER CUT AND WATER SALINITY IN AN OIL-WATER FLOW STREAM BY MEASURING THE SULFUR CONTENT OF THE PRODUCED OIL

CROSS-REFERENCE TO RELATED APPLICATIONS

The present application is an improvement on the subject matter of U.S. patent application Ser. No. 748,072, filed Dec. 6, 1976, and assigned to the assignee of the present invention but now abandoned.

BACKGROUND OF THE INVENTION

1. Field of Invention

The present invention relates to nuclear techniques for detecting water cut and water salinity in an oil/water flowstream in petroleum refining and producing operations.

2. Description of the Prior Art

U.S. patent application Ser. No. 748,072 relates to a new and improved method and apparatus for determining the presence of salt water in a fluid conduit, such as crude oil at a wellhead, loading dock or other location, or refined product, feed stock or waste water to dispose of at a refinery.

With this technique, the fluid is bombarded with fast neutrons from a neutron source which are slowed down and thereafter engage in thermal neutron capture reactions with materials in the fluid, giving rise to thermal neutron capture gamma rays. The energy spectra of the thermal neutron capture gamma rays are obtained, from which a measure of the relative presence of chlorine in the fluid may be ascertained, so that if the salinity of the fluid is known, the relative presence of salt water can accordingly be determined. Further, the relative presence of sulfur may under certain conditions be determined simultaneously with the relative presence of chlorine.

In many petroleum field applications, however, the produced fluid water salinity may vary. This is frequently the case in fields where water flooding (or steam flooding) with other than connate water is utilized. In these situations, the water cut of the salt water cannot be established unless corrections were made for salinity variations, which are difficult to quickly and accurately observe and determine.

SUMMARY OF INVENTION

Briefly, the present invention relates to a new and improved method and apparatus for determining the water cut of a liquid flowstream containing oil and water. The liquid flowstream may be at a wellhead or loading dock, feed stock in a refinery or waste water.

The liquid is bombarded with fast neutrons from a neutron source which are slowed down and thereafter engage in thermal neutron capture reactions with materials in the liquid, give rise to thermal neutron capture gamma rays. The energy spectra of the thermal neutron gamma rays are obtained, from which a measure of the concentration of chlorine, sulfur and hydrogen in the liquid may be ascertained.

In most oil fields, the sulfur content of the oil can be established to a high degree of accuracy and does not vary. With the present invention, the measures of the concentration of hydrogen, chlorine and sulfur and the established sulfur content of the oil are then used to obtain a measure of the oil cut of the liquid. From the measure of oil cut, the water cut of the liquid is obtained. As a further aspect of the present invention, the water salinity is determined from the water cut and the concentration of chlorine.

DESCRIPTION OF THE PREFERRED EMBODIMENT

The present invention is based upon the bombardment or irradiation with neutrons of a flowing stream of liquid, containing crude oil and water, and the detection of gamma radiation emitted by the elements chlorine, sulfur, and hydrogen upon capture of thermal neutrons. For a given thermal neutron flux, the yield of chemical element capture radiation is proportional to the concentration of that element in the flow stream. According to the present invention, since the sulfur content of crude oil during production is known to a high degree of accuracy and does not vary, the oil cut of the liquid is first ascertained from the concentration of sulfur in the liquid. The water cut of the liquid is then determined from the oil cut. Additionally, from the water cut and the concentration of chlorine, the water salinity of the liquid is determined.

Gamma radiation resulting from thermal capture $(n,\gamma)$ reactions is "prompt" in the sense that it is emitted within microseconds after the capture event. This is in contrast to "delayed" gamma radiation resulting from "activation" type reactions which is emitted from milliseconds to years after the reaction. Since thermal neutron capture radiation from prompt reactions is almost instantaneous, the velocity and volume flow rate of the crude oil stream do not affect the measurement. Another advantage of the present invention is that since thermal neutrons are required, a chemical source rather than an evacuated accelerator type neutron generator source can be used. Chemical sources are relatively inexpensive and, of course, require no associated electronics and maintenance.

Figure 1:
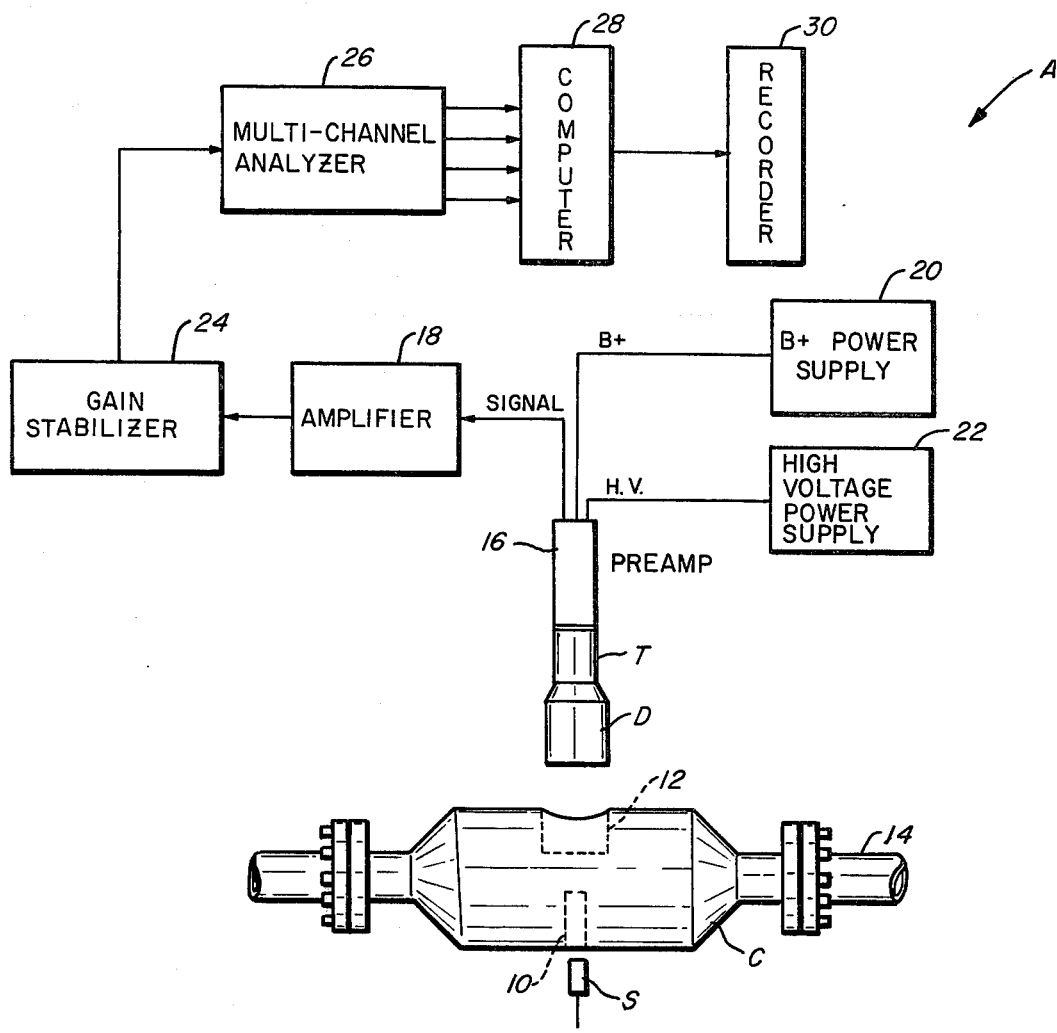
FIGS. 1 and 2 are schematic block diagrams of apparatus according to the present invention.

FIG. 1 shows an apparatus A according to the present invention with a neutron source S and a detector D mounted in suitable sockets 10 and 12, respectively, of a counting chamber C mounted in a crude oil flow line 14. The detector D is preferably a 5"×5" NaI(Tl) cylindrical crystal coupled to a photomultiplier tube T. The source S shown is a $Cf^{252}$ neutron source emitting $5 \times 10^7$ neutrons per second, although it should be understood that a different source material such as actinium-beryllium, americium-boron, or americium-beryllium could be used, if desired.

The chamber C preferably should be constructed of some material which contains no elements producing appreciable capture gamma radiation above 5.0 MeV. Aluminum or certain fiberglass-epoxy materials would be suitable, although iron, which produces 9.30 and 7.64 MeV gamma radiation through (n,γ) reactions, should be avoided. It should be noted that the chamber C is designed such that the detector D and source S are physically isolated in the sockets 10 and 12 from the crude oil. This eliminates the possibility of contaminating the crude oil if the source S should leak and also permits the detector D and source S to be removed without interrupting the flow of crude oil.

Figure 2:
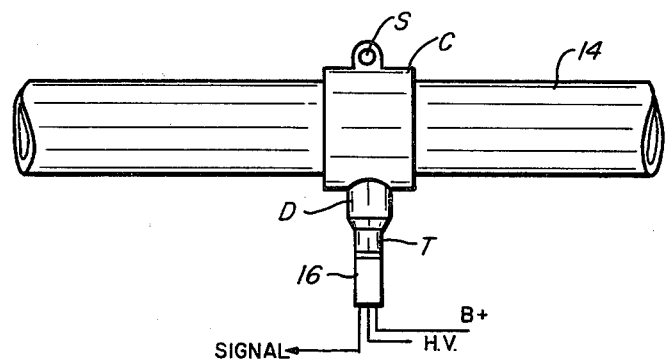

The physical shape of the chamber C is not critical as long as the source S and detector D are surrounded by at least several inches of liquid. FIG. 2 depicts an alternative configuration wherein both the source S and detector D are mounted external to the conduit 14. In certain situations, such as if iron is used to construct chamber C, it might be desirable to coat the inside of the chamber C with a durable material of high thermal neutron cross capture cross section, such as boron. This would reduce the thermal neutron interactions with the walls of the chamber and also prevent the escape from the chamber of thermal neutrons that might react with elements outside the chamber producing additional "background" radiation. Boron (boron carbide mixed with epoxy resin) would be ideal for this application since it has a large thermal neutron capture cross section ($\sigma = 775$ barns) and a capture reaction which produces no radiation above 5.0 MeV.

The detector D produces scintillations or discrete flashes of light whenever gamma rays pass therethrough, while the photomultiplier tube T generates in response to each such scintillation a voltage pulse proportional to the intensity of the scintillation. A conventional preamplifier circuit 16 amplifies the pulses from the photomultiplier tube T and furnishes the amplifier pulses to a further amplifier stage 18. A B+ power supply 20 is provided for the preamplifier 16, and a high voltage power supply 22 is provided for the photomultiplier tube T.

Figure 3:
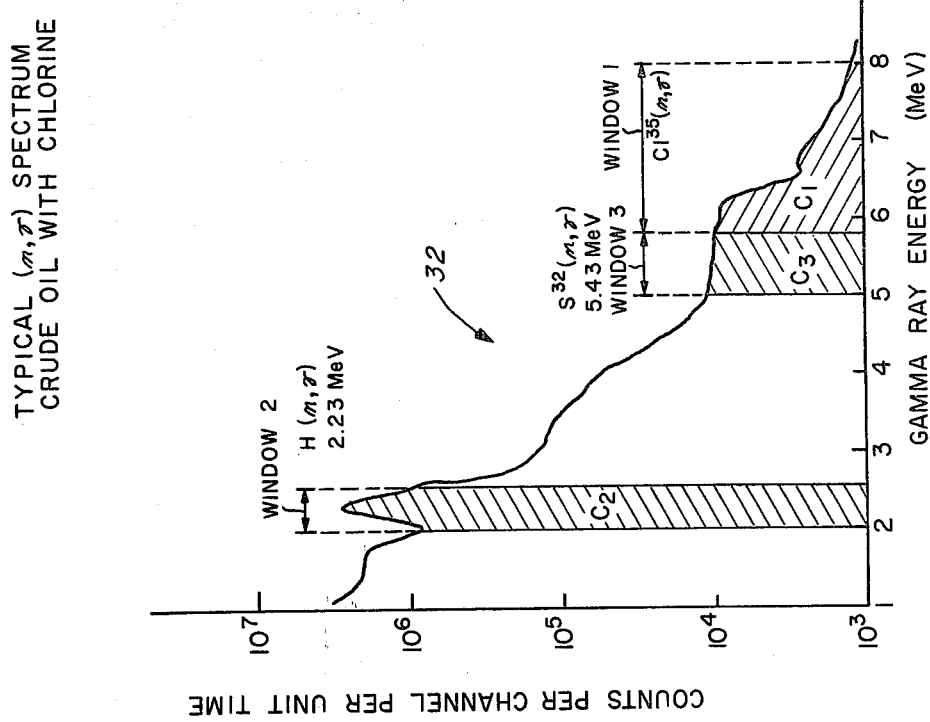
FIG. 3 is a graphical illustration of a typical thermal neutron capture gamma ray spectrum for a two phase flowstream containing water and crude oil.

The output pulses from the amplifier 18 are furnished to a gain stabilizer circuit 24 which is calibrated to respond to the energy level of a selected reference peak in the gamma ray energy spectrum, such as the 2.23 MeV energy peak of hydrogen in Window 2 (FIG. 3). It should be understood, however, that other gamma ray energy peaks or a peak generated by a light emitting diode mounted within detector crystal D or a peak from a mercury type pulser may be used for gain stabilization, if desired. The gain stabilizer circuit 24 is an automatic gain control circuit which responds to energy level of pulses at the calibrated peak level and adjusts the gain of all energy level pulses to compensate for gain shift or variations in tube T and other circuitry of the apparatus of the present invention due to power supply voltage fluctuations and/or temperature effects.

The output pulses from gain stabilizer circuit 24 are supplied to a pulse height or multi-channel analyzer 26. The pulse height analyzer 26 may be of conventional design as known in the art and having, for example, three or more channels or energy divisions corresponding to quantizations or energy ranges of the pulse heights of the input pulses, if desired. The pulse height analyzer 26 functions to sort and accumulate a running total of the incoming pulses into a plurality of storage locations or channels based on the height of the incoming pulses which, it will be recalled, is directly related to the energy of the gamma rays causing the pulse. The output of the pulse height analyzer 26 in the case of the present invention consists of count pulses occurring in each of three energy ranges or windows as depicted in FIG. 3. It should also be understood that three appropriately biased single channel analyzers may be used in place of the multi-channel analyzer 26, if desired.

The output from the pulse height analyzer 26 may be stored on a suitable memory device for subsequent processing, or alternatively, is supplied directly over an appropriate number of lines to a computer 28, which obtains from the number of chlorine, sulfur and hydrogen counts a measure of the oil cut and accordingly, the water cut, in the liquid in the line 14, in a manner to be set forth. Further, the computer 28 may also determine from the output of analyzer 26 a measure of the water salinity of such liquid. The results of such computations may be stored or displayed, as desired with a recorder 30 or other suitable display device.

FIG. 3 shows a typical capture gamma ray spectrum 32 recorded using the equipment of FIG. 1 for a stream of liquid crude oil containing oil and water. The intense peak of 2.23 MeV results from the capture of thermal neutrons by hydrogen in the crude oil and/or water and is used, as set forth above, as an energy reference peak by the gain stabilizer circuit of FIG. 1. FIG. 3 also shows the energy settings of the multi-channel analyzer 26. The first setting, identified as "Window 1", extends from 5.75 to 8.0 MeV and includes photoelectric and escape peaks from the 7.79, 7.42, 6.64 and 6.11 MeV radiation from the $Cl^{35}$ (n,γ) $Cl^{36}$ reaction as well as the relatively low intensity 7.78, 7.42, 7.19, 6.64 and 5.97 MeV peaks from sulfur. The second setting, identified as "Window 2", extends from 2.00 to 2.50 MeV and includes the 2.23 MeV hydrogen capture peak. The third setting, identified as "Window 3", extends from 5.00 to 5.75 MeV and includes the relatively intense 5.42 MeV sulfur capture peak.

DETERMINATION OF OIL CUT AND WATER CUT

At the outset, it is to be noted that the counts obtained in the apparatus A must be compensated in accordance with the sensitivity calculations in the manner set forth in the co-pending U.S. patent application discussed above. For the liquid in the flowstream 14, the following terms of nomenclature are applied:

$L_{oc}$ = fraction of the liquid that is oil, or oil cut
$L_{wc}$ = fraction of the liquid that is water, or water cut
$M_{cl}$ = concentration of salt (in pounds of NaCl per thousand barrels of liquid)
$M_S$ = concentration of sulfur in the liquid (%)
$M_{so}$ = concentration of sulfur in the oil phase of the liquid (%)
$C_H$ = counts accumulated in the hydrogen window (2)
$C_{Cl}$ = counts accumulated in the chlorine window (1)
$C_S$ = counts accumulated in the sulfur window (3)
$R_{Cl} = C_{Cl}/C_H$ ratio of counts in chlorine window (1) to counts in hydrogen window (2)
$R_S = C_S/C_H$ = ratio of counts in sulfur window (3) to counts in hydrogen window (2)
$m_i$ = constants (i = 1, ..., 4)
$b_j$ = constants (j = 1,2)

With the present invention, the computer 28 is utilized to determine $L_{wc}$ from the values $C_H$, $C_{Cl}$, and $C_S$ obtained in the analyzer 26. For a given sulfur concentration in a liquid, $M_{Cl}$ is a linear function of the ratio $R_{Cl}$. Therefore, $$M_{Cl} = m_1 R_{Cl} + y_1 \tag{1}$$

The y intercept of Equation 1, $y_1$, varies with sulfur concentration according to the Equation $$y_1 = m_2 M_S + b_1 \tag{2}$$

Substituting Equation (2) into Equation (1) yields $$M_{Cl} = m_1 R_{Cl} + m_2 M_S + b_1 \tag{3}$$

Also, for a given chlorine concentration, $M_s$ varies with $R_S$ according to the Equation $$M_S = m_3 R_S + y_2 \tag{4}$$

where $$y_2 = m_4 M_{Cl} + b_2 \tag{5}$$

Substituting Equation (5) into Equation (4) yields $$M_S = m_3 R_S + m_4 M_{Cl} + b_2 \tag{6}$$

Equations (3) and (6) can now be solved simultaneously for $M_{Cl}$ to yield $$M_{Cl} = K_1 + K_2 R_{Cl} + K_3 R_S \tag{7}$$

where $K_1$, $K_2$ and $K_3$ are calibration constants defined as follows:

$$K_1 = (m_2 b_2 + b_1)/(1 - m_2 m_4)$$
$$K_2 = m_1/(1 - m_2 m_4) \tag{8}$$
$$K_3 = m_2 m_3/(1 - m_2 m_4)$$

Likewise, Equations (3) and (6) can be solved simultaneously for $M_S$ to yield $$M_S = K_4 + K_5 R_S + K_6 R_{Cl} \tag{9}$$

However $$M_S = L_{oc} M_{so} \tag{10}$$

and $$L_{wc} = 1 - L_{oc} \tag{11}$$

Substituting Equation (10) into Equation (11) and solving for $L_{wc}$ yields to $$L_{wc} = 1 - (M_s/M_{so}) \tag{12}$$

Substituting Equation (9) into Equation (12) yields:

$$L_{wc} = 1 - (K_4 + K_5 R_S + K_6 R_{Cl}) M_{so}^{-1} \tag{13}$$

where $K_4$, $K_5$ and $K_6$ are calibration constants defined as follows:

$$K_4 = (m_4 b_1 + b_2)/(1 - m_2 m_4)$$
$$K_5 = m_3/(1\ m_2 m_4) \tag{14}$$
$$K_6 = m_1 m_4/(1 - m_2 m_4)$$

It should be noted that the K terms in Equations (8) and (14) contain only the constant terms $m_i$ and $b_j$. These constant terms are governed only by the physical and nuclear design of the apparatus A and are evaluated using a monitor calibration procedure. The ratios $R_{Cl}$ and $R_S$ are first measured using fluids containing known amounts chlorine ($M_{Cl}$) and sulfur ($M_S$) concentrations. These data are then used in Equations (1), (2), (4) and (5) along with least squares fitting techniques to obtain $m_i$ and $b_j$. Finally, the constants K are computed from the resulting values of $m_i$ and $b_j$ using Equations (8) and (14).

Test values for the constants K were obtained in accordance with the foregoing procedure for an apparatus A of the following configuration:

Source S: Am-B($1.16 \cdot 10^7$ n/sec)

Detector D: $3'' \times 3''$ NaI(T1) cylindrical crystal

Using oil as a base fluid containing varying amounts of chlorine (as $C_2H_2Cl_4$) and sulfur, the constants K were obtained for an apparatus A of the configuration set forth above as:

$$K_1 = 309.12$$
$$K_2 = 26,892$$
$$K_3 = -10,845$$
$$K_4 = -0.9646$$
$$K_5 = 531.62$$
$$K_6 = -357.13 \tag{15}$$

Figure 4:
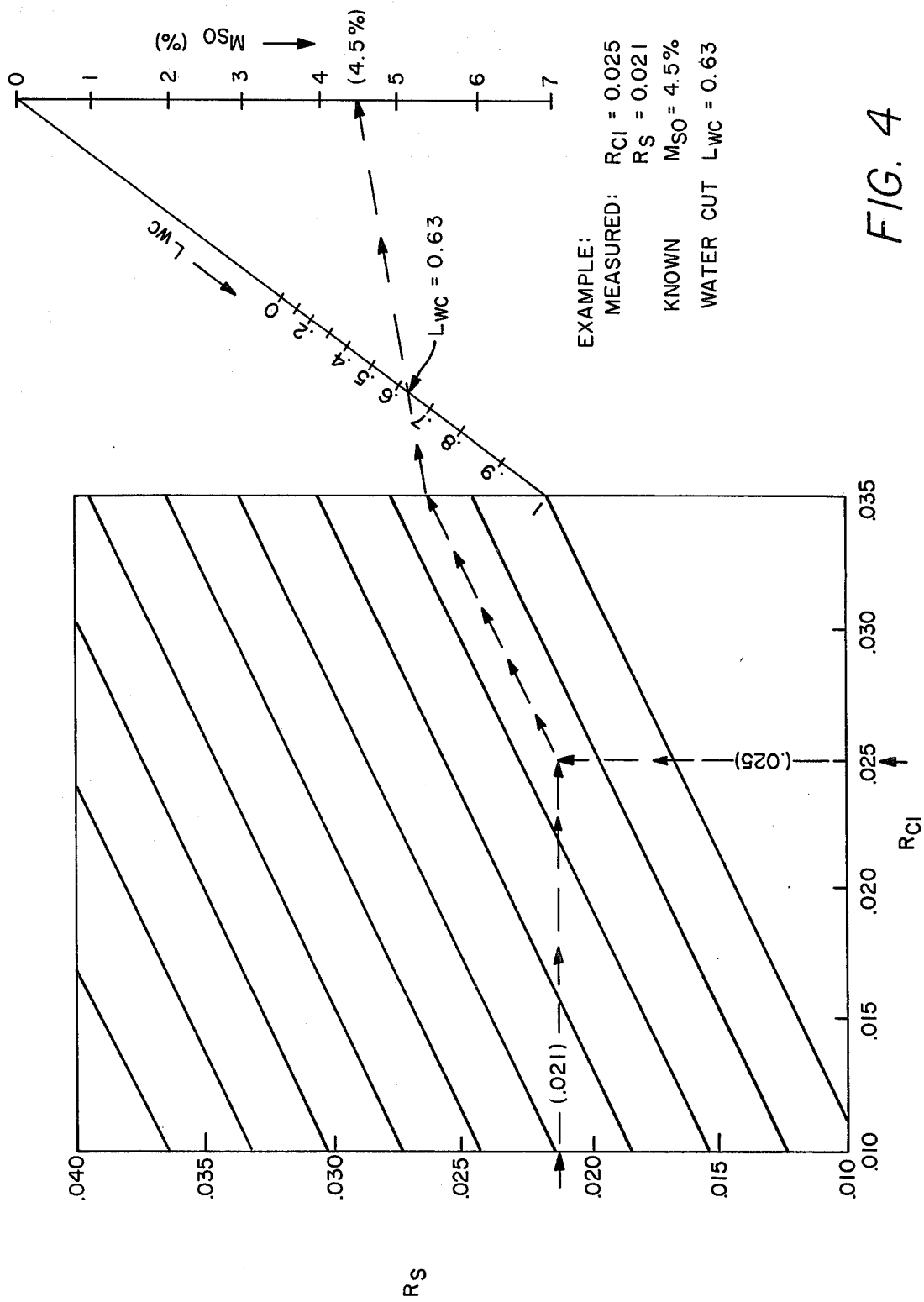
FIG. 4 is a graph by which the water cut of the fluid is determined for a fluid according to the present invention as a function of sulfur content, and the ratios chlorine neutron capture gamma ray count and sulfur neutron capture gamma ray count of the fluid, respectively, to the hydrogen neutron capture gamma ray count from the fluid.

Thus, it can be seen that these values of $K_4$, $K_5$ and $K_6$ are known calibration constants, and $M_{so}$ is a known value, representing the sulfur content of the crude oil in the liquid. The values of $R_S$ and $R_{Cl}$ are ratios determined in the computer 28 from the measured quantities $C_H$, $C_{Cl}$ and $C_S$. Using the measured quantities, $L_{wc}$, the water cut of the liquid, can, therefore, be determined using Equation (13). A nomograph is set forth in FIG. 4 exemplifying how the water cut $L_{wc}$ can be rapidly and accurately determined according to the present invention in the manner set forth above from the ratios $R_S$ and $R_{Cl}$ of the concentrations of sulfur and chlorine, respectively, to the concentration of hydrogen and the measured sulfur content $M_{so}$.

DETERMINATION OF WATER SALINITY

Further in accordance with the present invention, the chlorine count $C_{Cl}$ is utilized to determine the percent chlorine $P_{Cl}$ in the liquid in accordance with the relationship:

$$C_{Cl} = K_{Cl}' \cdot P_{Cl} \cdot T \tag{16}$$

where $K_{Cl}'$ is a calibration constant determined in the manner disclosed in the copending U.S. patent application referenced above, and T is the count time.

Figure 5:
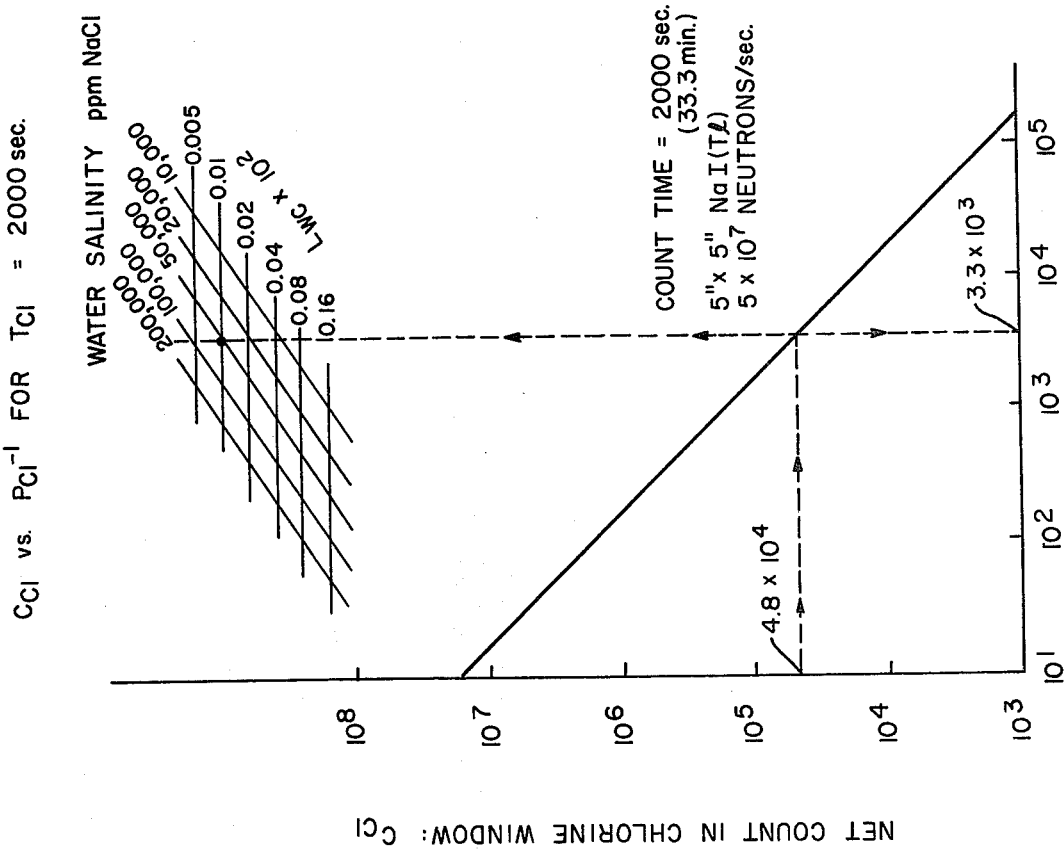
FIG. 5 is a graphical illustration of net counts of chlorine neutron capture gamma rays count as a function of percent chlorine in a fluid used to determine water salinity with the present invention.

Now that the chlorine count $C_{Cl}$, the percent chlorine $P_{Cl}$ in the liquid and the water cut $L_{wc}$ or percent water are known, the water salinity of the fluid may be determined assuming that all chlorine contained in the liquid is contained in the water in the form NaCl. FIG. 5 is a chart exemplifying hot water salinity can be accurately determined once the water cut $L_{wc}$ is determined in accordance with the present invention.

It should be understood that the techniques described above are not necessarily confined to a counting chamber geometry. In the event that the subject measurement must be made in a flow line without cutting the pipe or without diverting a portion of the stream to a counting chamber as described above, it would still be possible to make an estimation of the water cut and water salinity (albeit not as precise) by locating the source S and detector D against the pipe 14 on opposite sides of it.

The neutron source S and detector D would thus be mounted on the outside of the existing flow line 14 by means of a suitable clamp device C, or other suitable pipe attachment means, as shown in FIG. 2. The remainder of the apparatus of FIG. 2 corresponds to that of FIG. 1 and thus is not shown. However, this apparatus is connected to the preamplifier 16 and the photomultiplier tube T in the manner set forth above for FIG. 1. Measurements have been made indicating that ppm concentrations of chlorine and 0.1 percent concentrations of sulfur can be detected using this "through-pipe" technique of FIG. 2; however, for a given count time, the precision to which the through-pipe measurements can be made is not as good as that obtained using a counting chamber.

From the foregoing, it can be seen that the present invention provides a method of rapidly and accurately determining the water cut and water salinity of a fluid, even in circumstances where the water salinity is varying or fluctuating.

The foregoing disclosure and description of the invention are illustrative and explanatory thereof, and various changes in the size, shape and materials, as well as in the details of the illustrated construction may be made without departing from the spirit of the invention.

We claim:

1. A method for analysis of a liquid flowstream, containing oil and water and flowing in a conduit, to determine the water cut of the liquid, comprising the steps of:
   (a) bombarding the liquid with fast neutrons which are slowed down and thereafter engage in thermal neutron capture reactions with materials in the liquid;
   (b) obtaining gamma ray energy spectra of the materials in response to the capture of thermal neutrons by the materials in the liquid;
   (c) obtaining a measure of the concentration of chlorine, hydrogen and sulfur in the liquid from the gamma ray energy spectra; and
   (d) obtaining from the measure of the concentration of chlorine, hydrogen and sulfur, a measure of the water and oil cuts of the liquid.

2. The method of claim 1, wherein the liquid is feed stock in a petroleum refining conduit.

3. The method of claim 1, wherein the liquid is observed in a well head conduit at an oil well.

4. The method of claim 1, wherein the liquid is observed at a loading dock.

5. The method of claim 1, wherein the liquid is waste liquid which is to be disposed.

6. The method of claim 1, further including the step of:
   obtaining from the water cut and the measure of the concentration of chlorine in the liquid a measure of the salinity of the liquid.

7. The method of claim 1, wherein said step of obtaining gamma ray energy spectra includes:
   obtaining gamma rays from chlorine in the range of from 5.75 MeV to 8.0 MeV.

8. The method of claim 1, wherein said step of obtaining gamma ray energy spectra includes:
   obtaining gamma rays from sulfur in the range of from 5.0 MeV to 5.75 MeV.

9. The method of claim 1, wherein said step of obtaining gamma ray energy spectra includes:
   obtaining gamma rays from hydrogen in the range of from 2.0 MeV to 2.50 MeV.

10. The method of claim 1, wherein said first neutrons are emitted from a neutron source and further including the step of:
    attaching said neutron source to the conduit prior to said step of bombarding.

11. The method of claim 1, wherein said fast neutrons are emitted from a neutron source and further including the step of:
    inserting said neutron source into the conduit prior to said step of bombarding.

12. The method of claim 1, wherein said gamma ray spectra are obtained in a detector and further including the step of:
    inserting said detector into the conduit.

13. The method of claim 1, wherein said gamma ray spectra are obtained in a detector and further including the step of:
    attaching said detector to the conduit.

14. An apparatus for analysis of a liquid flowstream, containing oil and water and flowing in a conduit, to determine the water cut of the liquid, comprising:
    (a) means for bombarding the liquid with fast neutrons which are slowed down and thereafter engage in thermal neutron capture reactions with materials in the liquid;
    (b) means for obtaining gamma ray energy spectra of the materials in response to the capture of thermal neutrons by the materials in the liquid;
    (c) means for obtaining a measure of the concentration of chlorine, hydrogen and sulfur in the liquid from the gamma ray energy spectra; and
    (d) means for obtaining from the measure of the concentration of chlorine, hydrogen and sulfur, a measure of the water and oil cuts of the liquid.

15. The apparatus of claim 14, wherein said means for bombarding is mounted adjacent a petroleum refining conduit.

16. The apparatus of claim 14, wherein said means for bombarding is mounted adjacent a well head conduit at an oil well.

17. The apparatus of claim 14, wherein said means for bombarding is mounted adjacent a conduit at a loading dock.

18. The apparatus of claim 14, wherein said means for bombarding is mounted adjacent a conduit to bombard with neutrons waste liquid to be disposed.

19. The apparatus of claim 14, wherein said means for obtaining a measure of the water cut further includes:
    means for obtaining gamma rays from chlorine in the range of from 5.75 MeV to 8.0 MeV.

20. The apparatus of claim 14, wherein said means for obtaining gamma ray energy spectra includes:
    means for obtaining gamma rays from sulfur in the range of from 5.0 MeV to 5.75 MeV.

21. The apparatus of claim 14, wherein said means for obtaining gamma ray energy spectra includes:
    means for obtaining gamma rays from hydrogen in the range of from 2.0 MeV to 2.50 MeV.

22. The apparatus of claim 14, wherein said means for obtaining gamma ray energy spectra comprises:
    means for attaching said neutron source to the conduit.

23. The apparatus of claim 14, wherein said means for bombarding is attached to the exterior of said conduit.

24. The apparatus of claim 14, wherein said means for bombarding is inserted into said conduit.

25. The apparatus of claim 14, wherein said means for obtaining gamma ray spectra is attached to the exterior of said conduit.

26. The apparatus of claim 14, wherein said means for obtaining gamma ray spectra is inserted into the exterior of said conduit.

* * * * *